United States Patent [19]

Causse

[11] Patent Number: 5,370,689

[45] Date of Patent: Dec. 6, 1994

[54] METHOD OF IMPLANTING A MIDDLE EAR PROSTHESIS

[75] Inventor: Jean-Bernard Causse, Colombiers, France

[73] Assignee: Xomed-Treace, Inc., Jacksonville, Fla.

[21] Appl. No.: 919,045

[22] Filed: Jul. 23, 1992

[51] Int. Cl.⁵ .................................. A61F 2/18
[52] U.S. Cl. ........................... 623/10; 600/25; 606/151; 606/225
[58] Field of Search ............ 623/10; 600/25; 606/151, 228, 231, 222, 223, 225

[56] References Cited

U.S. PATENT DOCUMENTS

| | | |
|---|---|---|
| 2,665,692 | 1/1954 | L'Esperance ............ 606/222 |
| 3,196,462 | 7/1965 | Robinson ................. 623/10 |
| 3,566,413 | 3/1971 | Marquet . |
| 3,570,497 | 3/1971 | Lemole ................... 606/151 |
| 3,710,399 | 1/1973 | Hurst . |
| 3,711,869 | 1/1973 | Shea, Jr. . |
| 3,823,423 | 7/1974 | Mercandino . |
| 4,130,905 | 12/1978 | Mercandino . |
| 4,169,292 | 10/1979 | Grote . |
| 4,281,419 | 8/1981 | Treace . |
| 4,601,723 | 7/1986 | McGrew . |
| 4,624,672 | 11/1986 | Lenkauskas . |
| 4,655,776 | 4/1987 | Lesinski . |
| 4,957,507 | 9/1990 | Lenkauskas ............. 623/10 |

FOREIGN PATENT DOCUMENTS

| | | | |
|---|---|---|---|
| 0231162 | 8/1987 | European Pat. Off. ........ 623/10 |
| 0281958 | 8/1990 | Germany .................... 623/10 |

Primary Examiner—Paul Prebilic
Attorney, Agent, or Firm—Gipple & Hale

[57] ABSTRACT

The middle ear prosthesis includes an elongated link member having an eyelet portion at one end for connection to one of the auditory ossicles and an opposite posting end connectable to part of another auditory ossicle. A hitching member joined to the link member provides a vehicle for attaching the stapedial tendon to the link member to restore the beneficial effects of the stapedial reflex. Movement of the prosthesis and other remaining portions of the auditory ossicles is thus influenced by the stapedial tendon. The hitching member can be formed of a flexible filament or a relatively inflexible material.

4 Claims, 3 Drawing Sheets

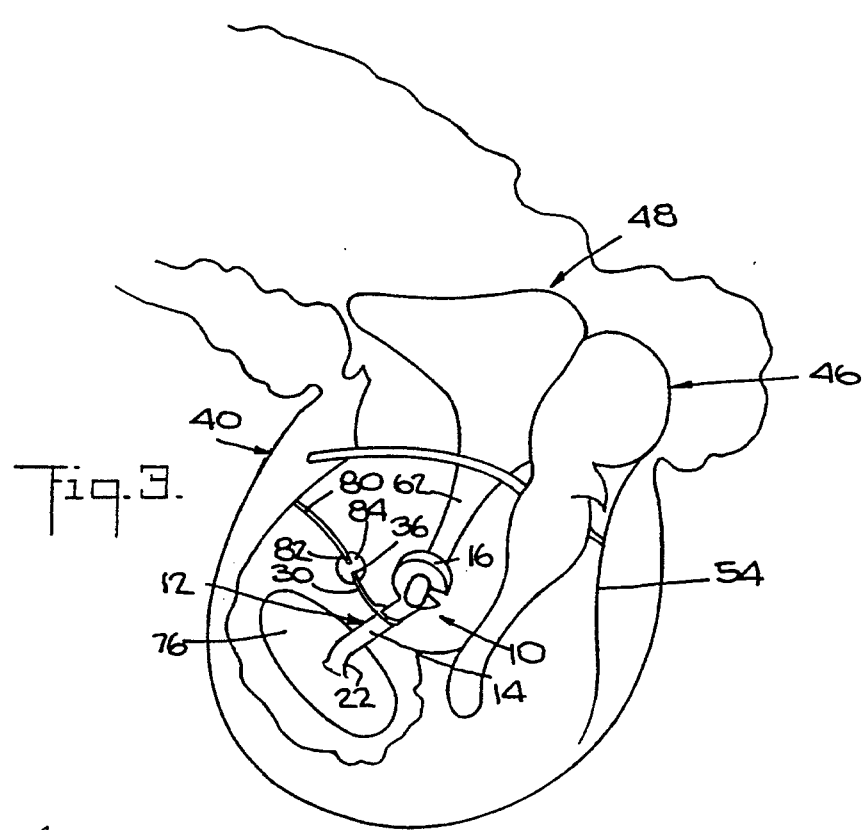
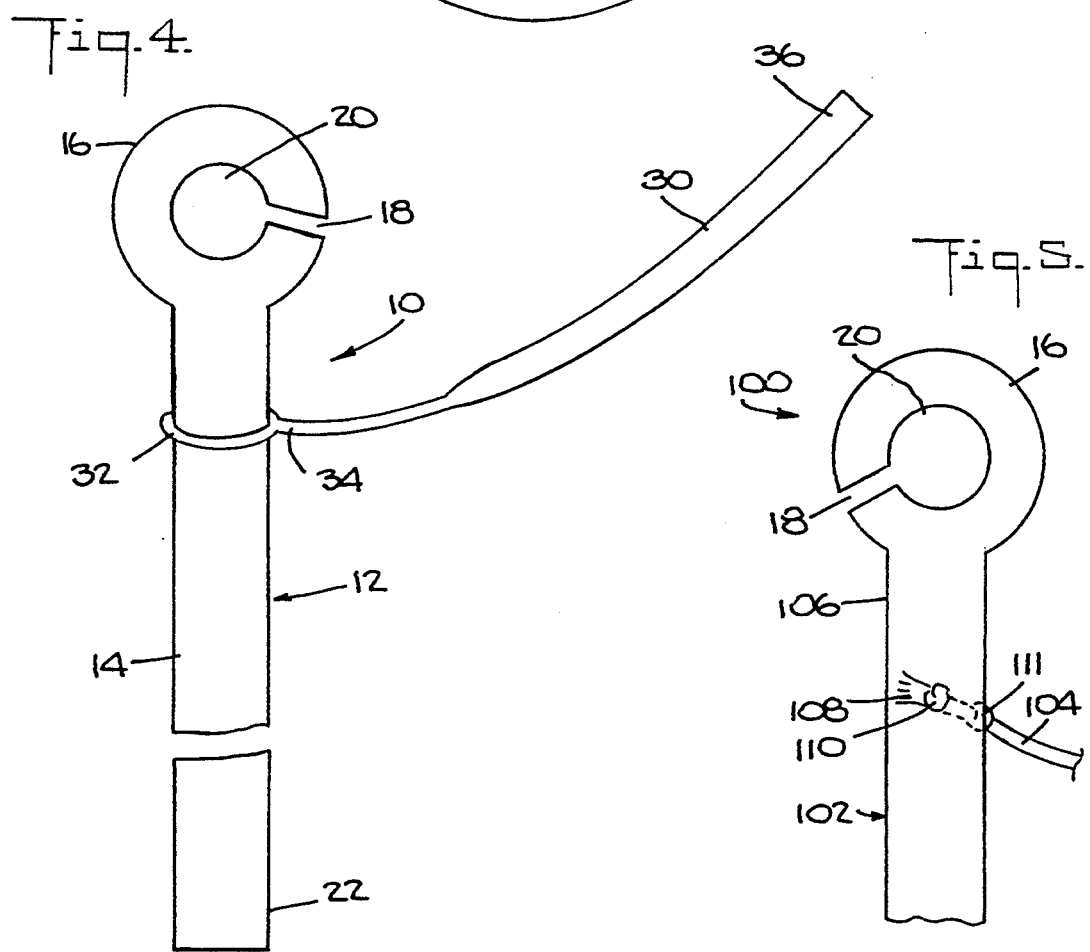

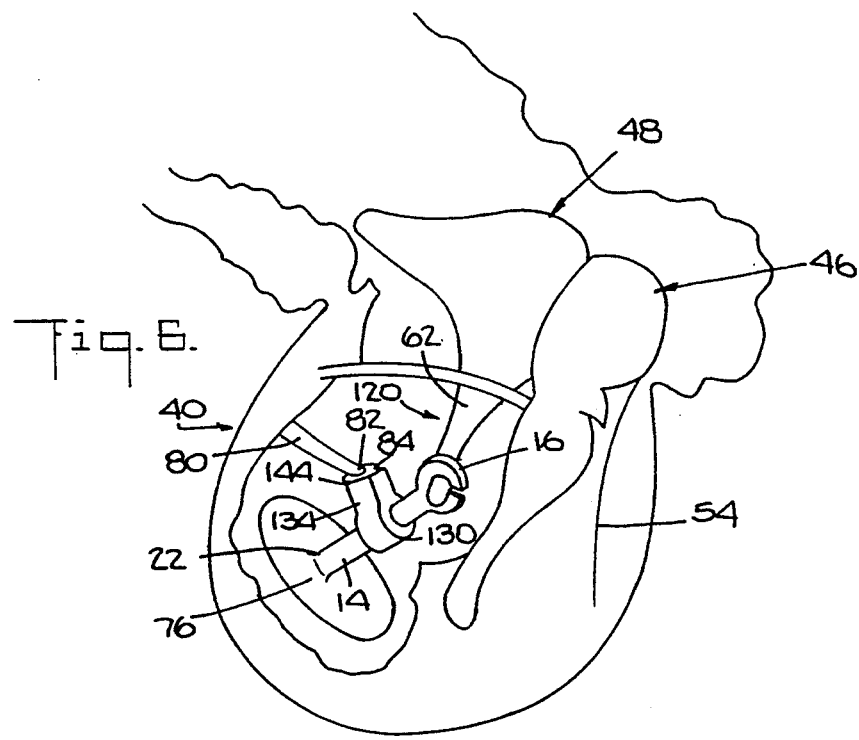
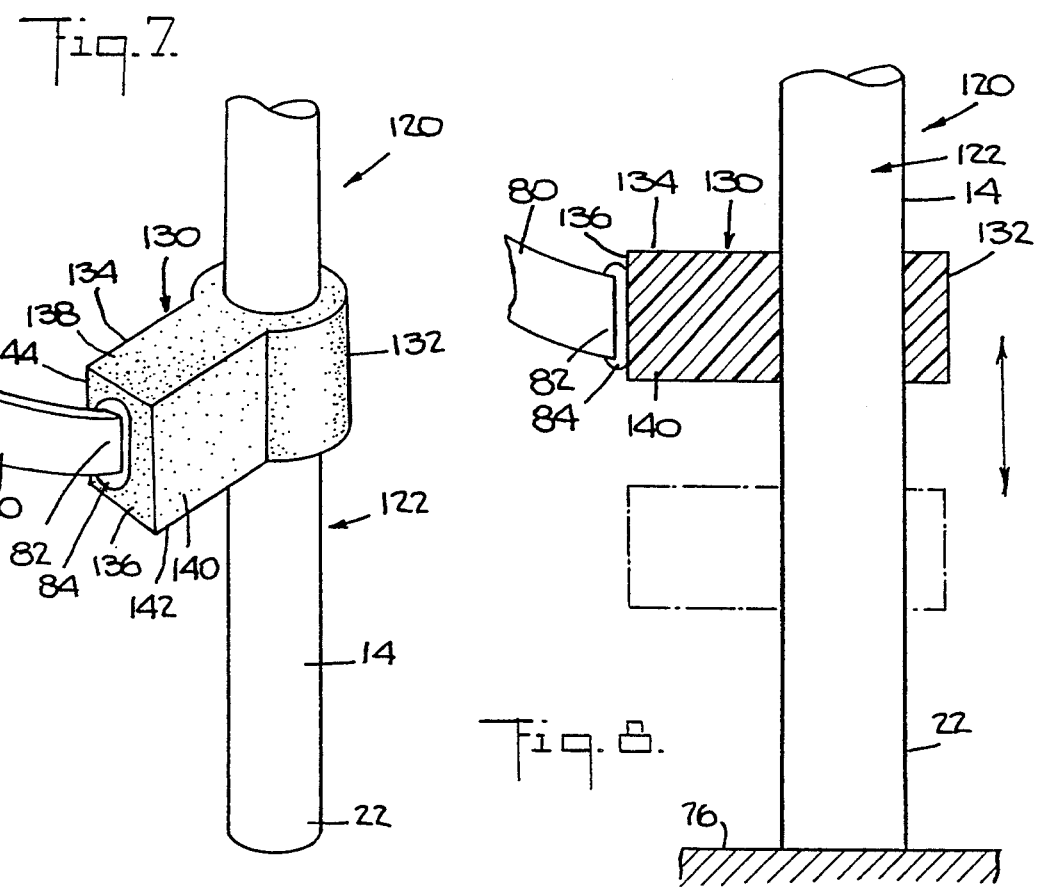

METHOD OF IMPLANTING A MIDDLE EAR PROSTHESIS

BACKGROUND OF THE INVENTION

This invention is directed to middle ear implants and more particularly to a novel middle ear prosthesis that responds to the stapedial reflex.

The middle ear transmits sound vibrations from the ear drum or tympanic membrane to the inner ear via auditory ossicles or movable bones that are linked together and known as the malleus, the incus and the stapes. The malleus, which is the outermost bone, is embedded in the tympanic membrane and connected to the incus, which is the middle bone. The stapes, which is the innermost bone, is connected to the incus and attached to the cochlea or inner ear at the margin of an oval window of the cochlea.

Optimum transmission of sound from the outer ear to the inner ear requires effective contact between the malleus and the tympanic membrane to sense sound induced vibrations of the tympanic membrane, functional movement of the malleus, the incus and the stapes in response to the vibrations of the tympanic membrane, and effective contact between the stapes and the cochlea to transmit sound vibrations to the inner ear.

Diseases of the middle ear such as otosclerosis or congenital ear defects can fix the stapes. The stapes is usually removed and replaced by a piston and often by a piece of vein graft in order to restore desirable vibration of the inner ear fluids. The impedance transfer and acoustic impedence of the annular ligament are the two main biophysical parameters to restore.

While much attention has been directed to functional replacement of the auditory ossicles, very little has been done to restore the function of the stapedial tendon which is normally attached to the stapes. The stapedial tendon is usually severed or detached when the stapes superstructure is removed or degenerated from disease. I have found that the stapedial reflex, which causes contraction of the stapedial tendon and consequential movement of the stapes footplate, plays a significant role in speech recognition.

The stapedial tendon is known to have a variable response to noise depending upon sound intensity, much like the iris has a variable response to different light intensities. The stapedial tendon retracts under loud sound impingement to reduce the amount of movement transmitted to the oval window of the cochlea by the stapes. Retraction of the stapedial tendon also raises the resonant frequency of the auditory ossicles and attenuates sound. The stapedial reflex thus helps guard against acoustic trauma to the ear.

My findings indicate that the stapedial reflex function is instrumental in the area of sound discrimination when several different people are speaking. Through the action of the stapedial tendon it is possible that high frequency tones are more easily discriminated and voices can be distinguished or enhanced in a noisy setting.

Detachment of the stapedial tendon from the stapes upon surgical removal of the stapes superstructure prevents retraction of the stapes footplate by the stapedial tendon. The beneficial effects of the stapedial reflex in influencing stapes footplate movement are thus lost.

It is thus desirable to provide a middle ear prosthesis that permits restoration of the stapedial reflex function to influence movement of the stapes footplate and selectively change the resonant frequency of nonremoved auditory ossicles.

OBJECTS AND SUMMARY OF THE INVENTION

Among the several objects of the invention which may be noted are the provision of a novel middle ear prosthesis, a novel middle ear prosthesis which can be hitched to a detached or severed stapedial tendon, a novel middle ear prosthesis that helps restore the function of the auditory ossicles and the stapedial tendon, and a novel method of restoring middle ear function.

Other objects and features of the invention will be in part apparent and in part pointed out hereinafter.

In accordance with the invention, the middle ear prosthesis includes an elongated link member that replaces a diseased or degenerated stapes superstructure which is surgically removed. The link member has an attachment joint at one end in the form of an eyelet for connection to the long crus of the incus. An opposite posting end of the link member is anchored onto or in the stapes footplate. The implanted link member transmits movement of the malleus and the incus to the stapes footplate in response to vibrations of the tympanic membrane.

The prosthesis further includes a hitching member joined to the link member. The hitching member includes an attachment portion attachable to the stapedial tendon to communicate movement of the stapedial tendon to the stapedial footplate through the link member. Stapedial reflex movement is thus applied to the link member to influence movement of the stapedial footplate. Stapedial movement of the link member also influences movement of the incus and malleus, thereby changing the resonant frequency of the remaining auditory ossicles.

In one embodiment of the invention, the hitching member includes a flexible elongated filament that is looped around the link member and attached to the stapedial tendon. In another embodiment of the invention the flexible filament is passed directly through a shaft portion of the link member and knotted for securement to the link member.

In a further embodiment of the invention the hitching member is formed of a relatively inflexible material and is joined to the link member via a collar portion that receives the shaft of the link member. The relatively inflexible hitching member includes an arm portion extending from the collar portion away from the link member. The arm portion includes at least one attachment surface onto which the stapedial tendon is joined.

Whether the hitching member is flexible or inflexible, the junction between the stapedial tendon and the hitching member permits communication of stapedial tendon movement to the prosthesis to obtain the beneficial effects of the stapedial reflex on the remaining auditory ossicles.

Middle ear function which has been impaired by deterioration of the stapes and detachment of the stapedial tendon from the stapes is thus remedied by joining the stapedial tendon to the hitching member of the prosthesis and implanting the prosthesis between the stapedial footplate and the incus.

The invention accordingly comprises the constructions and method hereinafter described, the scope of the invention being indicated in the claims.

DESCRIPTION OF THE DRAWINGS

In the accompanying drawings,

FIG. 3 is a view similar to FIG. 2, including a middle ear prosthesis incorporating one embodiment of the present invention, the prosthesis being disposed between the incus and the stapes footplate and joined to the stapedial tendon;

FIG. 4 is an enlarged detail view of the middle ear prosthesis;

FIG. 5 is an enlarged elevated view of another embodiment of the middle ear prosthesis;

FIG. 6 is a view similar to FIG. 2, showing a further embodiment of the middle ear prosthesis;

FIG. 7 is an enlarged fragmentary perspective view thereof; and,

FIG. 8 is a fragmentary elevation view thereof, partly shown in section.

Corresponding reference characters indicate corresponding parts throughout the several views of the drawings.

DETAILED DESCRIPTION OF THE INVENTION

Figure 1:
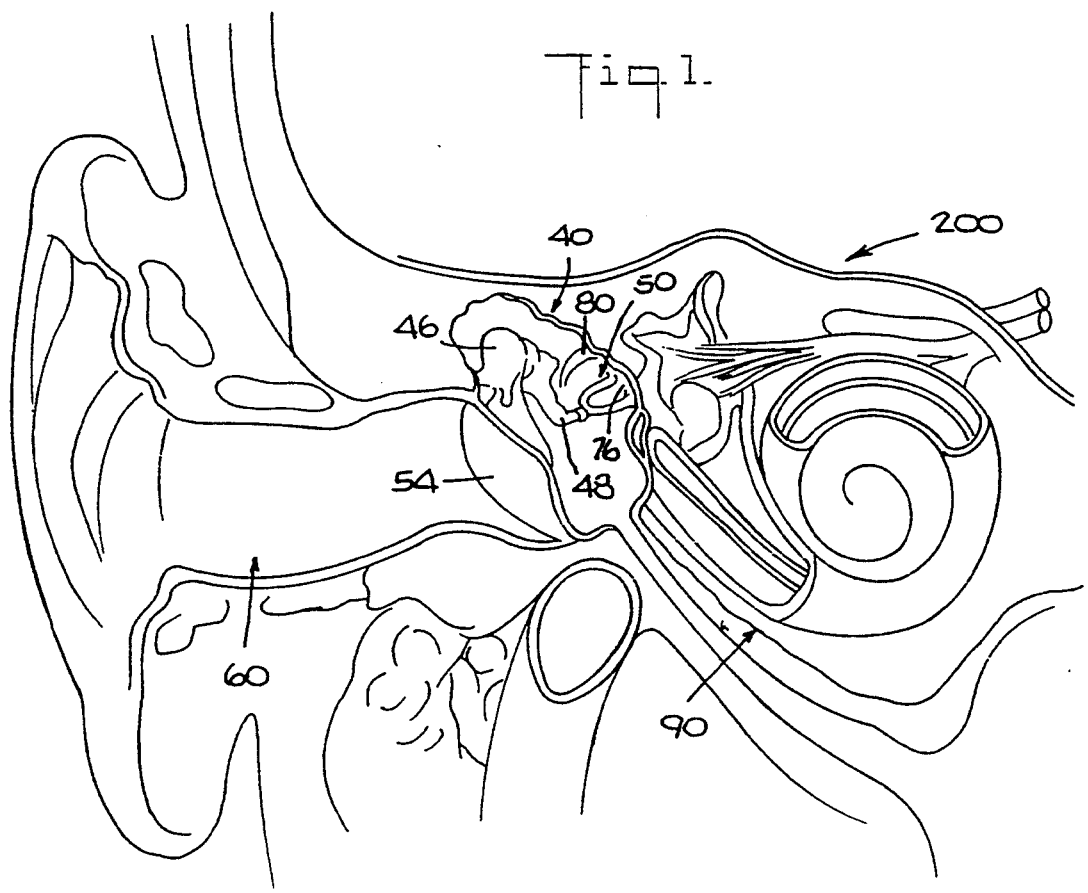
FIG. 1 is a simplified cutaway frontal view of the outer ear, the middle ear and the inner ear.

A middle ear prosthesis incorporating one embodiment of the invention is generally indicated by the reference number 10 in FIGS. 3 and 4.

The prosthesis 10 comprises a link member 12 made of a suitable biocompatible material such as polytetrafluoroethylene and an adjoining hitching member 30. The link member 12 includes an elongated shaft portion 14 with an eyelet 16 at one end and an opposite posting end 22. The eyelet 16, which is split at 18, defines an opening 20.

The elongated hitching member 30, which is a flexible filament, can be formed of platinum, titanium or stainless steel wire having a diameter of approximately 0.005 inches, for example. A loop 32 provided at an end 34 of the hitching member 30 tightly encircles the shaft 14 and is thus affixed to the shaft 14. The loop 32 is located a predetermined distance from the eyelet portion 16 and can be preformed before attachment to the shaft 14 or formed by wrapping the hitching member 30 around the shaft 14. Preferably the wire filament of the hitching member 30 is flattened and crimped as shown in FIG. 4 to promote attachment to the body tissue.

Figure 2:
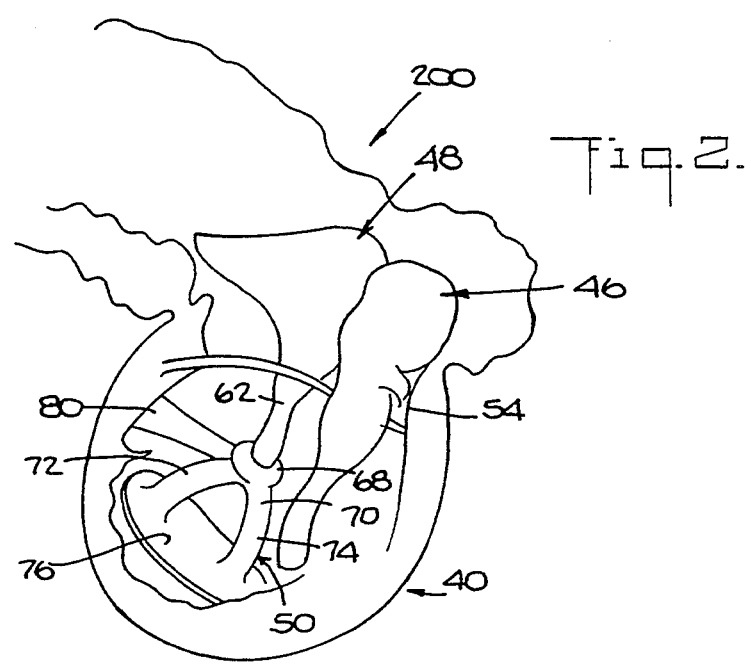
FIG. 2 is an enlarged simplified perspective view of the tympanic cavity or middle ear including the auditory ossicles.

In a normal ear 200, as shown schematically in FIGS. 1 and 2, a linkage of auditory ossicles in a middle ear portion 40 includes a malleus 46, an incus 48 and a stapes 50. The malleus 46, which is the outermost auditory ossicle, joins the tympanic membrane or eardrum 54, and is also joined to the incus 48. The stapes 50 includes a head portion 68 joined to a long crus 62 of the incus 48. The stapes 50 also includes a neck portion 70 adjacent the head portion 68, a posterior crus 72 and an anterior crus 74 that join a stapes footplate 76. The head portion 68, the neck portion 70, the posterior crus 72 and the anterior crus 74 are also known as the stapes superstructure.

Within the middle ear 40, a stapedial tendon 80 is attached to the neck 70 of the stapes 50 at the posterior crus 72. The stapedial tendon 80 extends into a bony cavity (not shown) of the middle ear 40 to join the stapedius muscle (not shown) which is enervated by a branch of the facial nerve (not shown).

If a middle ear disease infects or destroys parts of the stapes superstructure 68, 70, 72 and 74, a loss of hearing results and removal of the infected stapes superstructure is often recommended. During surgical removal of the stapes superstructure, the stapedial tendon 80 is usually severed or is detached from the stapes 50 as a result of disease. The stapedial tendon 80 is thus unable to perform its beneficial functions of influencing movement of the stapes footplate 76 and changing the resonant frequency of the auditory ossicles.

Installation of the prosthesis 10 following surgical removal of the stapes superstructure 68, 70, 72 and 74, includes positioning the link member 12 as shown in FIG. 3 to engage the long crus 62 of the incus 48, at the eyelet portion 16. The eyelet 16 is tightened around the long crus 62 with a suitable clamping tool such as a cupped forceps (not shown). The posting end 22 of the shaft 14 is joined to the stapes footplate 76 by, for example, drilling a hole in the footplate and using a vein graft to secure the position of the posted end 22 in the drilled hole. In this manner the prosthesis 10 is linked to the incus 48 and the stapes footplate 76. Movement of the malleus 46 and the incus 48 in response to vibrations of the tympanic membrane 54 is thus communicated to the stapes footplate 76 through the link member 12.

The stapes footplate 76, which is attached to the oval window (not shown) of the inner ear or cochlea 90 (FIG. 1), transmits sound from the middle ear 40 containing the prosthesis 10 to the inner ear 90.

Stapedial movement of the prosthesis 10 is accomplished by attaching a free end 36 of the hitching member 30 to a free end portion 82 (FIG. 3) of the stapedial tendon 80 that was severed or detached during surgical removal of the stapes superstructure 68, 70, 72 and 74. As shown in FIG. 3, a good connection is obtained by, for example, placing a fragment of perivenous connective tissue 84 between the free end 82 of the stapedial tendon 80 and the free end 36 of the hitching member 30.

The length of the hitching member 30 between the shaft 14 and the stapedial tendon 80 is predetermined to enable retractive movement of the stapedial tendon 80 to pull the hitching member 30 thereby moving the link member 12. Retractive movement of the stapedial tendon 80 thus influences movement of the stapes footplate 76 in a manner which mimics footplate movement that would normally result from a direct connection between the stapedial tendon 80 and a functional stapes 50 as shown in FIG. 2.

The precise dimensions of the prosthesis 10 may vary since they are based upon the dimensional characteristics of the middle ear which are known to differ with different patients. Nevertheless, to exemplify the magnitudes being dealt with, the overall length of the link 12 can be approximately 4.5 mm. to 6 mm. and the inside diameter of the eyelet can be approximately 0.3 mm. to 0.8 mm. The cross sectional diameter of the link can be approximately 0.6 mm. to 0.8 mm.

Another embodiment of the middle ear prosthesis is generally indicated by the reference number 100 in FIG. 5. The prosthesis 100 includes a link member 102 similar to the link member 12 and a hitching member 104 formed of the same material as the hitching member 30. The hitching member 104 is connected to a shaft portion 106 of the link member 102 by passing an end portion 108 of the hitching member 104 directly through the shaft 106. The end portion 108 of the hitching member 104 is knotted, as indicated at 111, at opposite sides of the shaft 106 to prevent relative movement between the hitching member 104 and the shaft 106.

The prosthesis 100, in all other respects, is similar in structure and operation to the prosthesis 10 and is installed in a manner similar to that previously described for the prosthesis 10.

A further embodiment of the middle ear prosthesis is generally indicated by the reference number 120 in FIGS. 6–8. The prosthesis 120 includes a link member 122 similar to the link member 12 with the shaft 14, the eyelet 16, and the posting end 22. A relatively inflexible hitching member 130 is joined to the shaft 14.

The hitching member 130 can be formed of a suitable biocompatible plastic or ceramic material such as hydroxylapatite which promotes tissue ingrowth or attachment. A collar portion 132 is provided at one end of the hitching member 130 to tightly receive the shaft 14 of the link 122. The hitching member 130 also includes an arm portion 134 that extends away from the collar portion 132. The arm portion 134 is generally rectangular in cross section having a free end attachment surface 136, as most clearly shown in FIG. 7.

Although the collar portion 132 tightly receives the shaft 14 of the link member 122, the hitching member 130 can be adjusted to a selected height relative to the eyelet portion 16, in the manner indicated in FIG. 8. The predetermined tightness between the collar portion 132 and the shaft 14 is sufficient to ensure that there is no unintended axial or rotational movement of the collar portion 132 relative to the shaft 14 after implantation occurs.

The link member 122 is connected to the incus 48 and posted in the stapes footplate 76 in a manner similar to that previously described for the prosthesis 10. The free end portion 82 of the stapedial tendon 80 is joined to the attachment surface 136 of the arm portion 134, but can also be joined to any of the other attachment surfaces 138, 140, 142 or 144. A bond between the stapedial tendon 80 and the attachment surface 136 can be enhanced with fibrin glue and/or a fragment of perivenous connective tissue 84.

The point at which the stapedial tendon 80 is attached to the attachment surface 136 is predetermined to ensure that the stapedial reflex, which causes retractive movement of the stapedial tendon 80, influences movement of the link 122. Movement of the link 122 by the stapedial tendon 80 is intended to mimic stapedial movement of the stapes 50 which was surgically removed.

Some advantages of the invention evident from the foregoing description include a middle ear prosthesis that replaces the stapes superstructure and cooperates with the stapedial tendon to obtain the beneficial effects of the stapedial reflex. A further advantage is the employment of a hitching member that connects with the stapedial tendon to restore stapedial movement of the auditory ossicles.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A method of restoring middle ear function which has been impaired by deterioration of the stapes and detachment of the stapedial tendon from the stapes comprising,
    a) joining one end of a link member to the long crus of the incus,
    b) posting an opposite end of the link member in the footplate of the stapes,
    c) attaching one end of a hitching member to the link member and another portion of the hitching member to the stapedial tendon, to permit retractive movement of the stapedial tendon to pull the hitching member and move the link member such that the stapes footplate moves in response to retractive movement of the stapedial tendon.

2. The method as claimed in claim 1 including looping the hitching member around the link member to attach the hitching member to the link member.

3. The method as claimed in claim 1 including passing the hitching member through the link member to attach the hitching member to the link member.

4. The method as claimed in claim 1 including forming the hitching member of an inflexible material with an inflexible arm portion and then collaring the hitching member on the link member such that the arm portion extends away from the link member, and attaching the stapedial tendon to the arm portion.

* * * * *